US005693752A

United States Patent [19]

Katinger et al.

[11] Patent Number: 5,693,752

[45] Date of Patent: Dec. 2, 1997

[54] PEPTIDES THAT INDUCE ANTIBODIES WHICH NEUTRALIZE GENETICALLY DIVERGENT HIV-1 ISOLATES

[75] Inventors: Hermann Katinger, Helligenstadterstr. 127 A/7/8, 1190 Wien; Florian Rüker; Gottfried Himmler, both of Vienna; Thomas Muster, Graz; Alexandra Trkola, Vienna; Martin Purtscher, Vienna; Georg Maiwald, Vienna; Franz Steindl, Vienna, all of Austria

[73] Assignee: Hermann Katinger, Vienna, Austria

[21] Appl. No.: 361,479

[22] Filed: Dec. 22, 1994

Related U.S. Application Data

[63] Continuation of Ser. No. 932,787, Aug. 29, 1992, abandoned.

[30] Foreign Application Priority Data

May 14, 1992 [AT] Austria .................................... 987/92

[51] Int. Cl.[6] .......................... A61K 38/04; A61K 39/21; A61K 39/38; C07K 5/00

[52] U.S. Cl. ....................... 530/329; 530/350; 424/208.1; 424/184.1; 424/188.1; 424/204.1

[58] Field of Search ............................ 424/184.1, 188.1, 424/192.1, 204.1, 208.1; 536/23.1, 23.4; 530/350, 329

[56] References Cited

FOREIGN PATENT DOCUMENTS

| | | | |
|---|---|---|---|
| 0330359 | 8/1989 | European Pat. Off. .......... | C07K 7/08 |
| 0 570 357 | 11/1993 | European Pat. Off. . | |
| 8707616 | 12/1987 | WIPO .............................. | C07K 7/08 |

OTHER PUBLICATIONS

Masayoshi Enami et al., Proc. Natl. Acad. Sci., Introduction of site-specific mutations . . . , vol. 87, pp. 3802–3805, May 1990.

Jamie K. Scott et al., Science, Searching for Peptide Ligands with an Epitope Library, vol. 249, pp. 386–390.

D.C. Wiley et al., Nature, Structural identification of the antibody-binding sites . . . , vol. 289, Jan. 29, 1981, pp. 373–378.

Johann Kohl et al., Annals of the New York Academy of Sciences, Cloning and Expression of an HIV-1 . . . , vol. 646, 1991, pp. 106–114.

D. McPhee et al., Recognition of envelope . . . , FEBS Letters, vol. 233, No. 2, Jun. 1988, pp. 393–396.

Science, Javaherian et al., Broadly neutralising antibodies . . . . , vol. 250, No. 4987, Dec. 14, 1980, pp. 1590–1593.

Nature, Evans et al., An engineered poliovirus . . . , vol. 339, No. 6223, Jun. 1, 1989, pp. 385–388.

AIDS, Vanini et al., Discrete regions of . . . , vol. 7, No. 2, Feb. 1993, pp. 167–174.

8th International Conference on AIDS Jul. 19–24, 1992, M. Purtscher et al., Human monoclonal antibodies . . . , vol. 8, No. 2.

AIDS Research and Human Retroviruses, V. Teeuwsen, Production and characterization . . . , vol. 6, No. 3, Mar. 1990. p. 381.

Cloning and Characterization of Human Immunodeficiency Virus Type I Variants Diminished in the Ability to Induce Syncytium-Independent Cytolysis by M. Stevenson et al., Journal of Virology, Aug. 1990, pp. 3792–3803 (vol. 64).

Complete nucleotide sequence of the AIDS virus, HLTV-III by Lee Ratner et al., Nature vol. 313, 24 Jan. 1985, pp. 277–284.

Computer-Assisted Analysis of Envelope Protein Sequences of Seven Human Immunodeficiency Virus Isolates: Prediction of Antigenic Epitopes in Conserved and Variable Regions by Susanne Modrow et al., Journal of Virology, Feb. 1987, pp. 570–578 (vol. 61).

Cohen, 1993, "Jitters Jeopardize . . . " Science 262:980–981.

Looney et al, 1988, "Type-restricted neutralization . . . " Science 241:357–359.

Weiss, et al, 1986, "Variable and conserved . . . " Nature, 324:572–575.

Palker, et al, 1988, "Type-Specific Neutralization of the . . . " PNAS 85:1932–1936.

Matsushita, et al, 1988, "Characterization of a human . . . " J. Virol. 62(6):2107–2114.

Broliden, et al, 1992, "Identification of human . . . " PNAS 89:461–465.

T. Muster et al. (1993) *Journal of Virology* 67:6642–6647.

T. Muster et al. (1994) *Journal of Virology* 68:4031–4034.

A. Robert Neurath et al. (1990) *Journal of General Virology* 71:85–95.

Thomas P. Hopp et al. (1981) *Proc. Natl. Acad. Sci. USA* 78:3824–3828.

Jian-Yin Xu et al. (1991) *Journal of Virology* 65:4832–4838.

Anthony J. Conley et al. (1994) *Proc. Natl. Acad. Sci. USA* 91:3348–3352.

*Primary Examiner*—Lynette F. Smith

*Attorney, Agent, or Firm*—Birch, Stewart, Kolasch & Birch, LLP

[57] ABSTRACT

This invention refers to peptides binding to antibodies that show neutralizing activity against different strains and clinical isolates of HIV-1 and that inhibit the fusion of cells caused by HIV-1. These peptides are applied with an adjuvant, as recombinant fusion proteins, chemically coupled to carrier molecules, as recombinant chimeric viruses or as recombinant antibodies.

13 Claims, 5 Drawing Sheets

Determination of peptide specific antibody titers in sera of HIV-I infected persons Influenza/HIV inhibition of HIV-1 IIIB neutralization

| monoklonal antibodies: | residual IIIB neutralizationstiter in% after inkubation with: | | |
|---|---|---|---|
| | Mock | Influenza WSN | Influenza/HIV |
| 2F5 | 100% | 100% | 10% |
| 2G12 | 100% | 100% | 100% |

| Immunogen: | Antibodytiter: |
|---|---|
| K1 | < 10 |
| K2 | < 10 |
| K3 | < 10 |
| F1 | 1600 |
| F2 | 6400 |
| F3 | 800 |
| SM1 | 3200 |
| SM2 | 400 |
| SM3 | 800 |
| V1 | 3200 |
| V2 | 3200 |
| V3 | 6400 |
| rA1 | < 10 |
| rA2 | 400 |
| rA3 | 800 |

FIG. 3b

Reciprocal neutralization titers of HIV-1 isolates

| Antiserum | IIIB | RF | MN |
|---|---|---|---|
| P1 | 40 | 40 | 40 |
| P2 | 80 | 40 | 40 |
| P3 | 40 | 20 | 20 |
| V1 | 40 | 80 | 40 |
| V2 | 20 | 40 | <10 |
| V3 | 160 | 80 | 80 |
| SM1 | 20 | 40 | 40 |
| SM2 | 40 | 80 | 80 |
| SM3 | <10 | <10 | <10 |
| rA1 | 40 | 40 | 40 |
| rA2 | 40 | 80 | 20 |
| rA3 | 80 | 40 | 40 |

FIG. 3c

PEPTIDES THAT INDUCE ANTIBODIES WHICH NEUTRALIZE GENETICALLY DIVERGENT HIV-1 ISOLATES

This application is a continuation of application Ser. No. 07/932,787 filed on Aug. 29, 1992, now abandoned.

FIELD OF THE INVENTION

This invention refers to peptides that induce antibodies which neutralize genetically divergent HIV-1 isolates. These peptides are applied with an adjuvant, as recombinant fusion proteins, chemically coupled to carrier molecules, as recombinant chimeric viruses or as recombinant antibodies. In addition, the stage of infection can be determined and the progression of the infection can be predicted with these peptides.

INTRODUCTION

The aquired immunodeficiency syndrome (AIDS) is the late stage clinical manifestation of long term persistent infection with human immunodeficiency virus type 1 (HIV-1). Immune responses directed against the virus and against virus-infected cells during the persistent infection usually fail to mediate resolution to the infection. A possibility to elicit an immune response that can prevent the establishment of a persistent infection or that can prevent the progression to AIDS are vaccines. Most vaccine strategies against HIV-1 are directed against the surface glycoprotein gp160 which is made up of gp120 and gp41 and is responsible for virus binding to the cellular receptor CD4 and fusion activity.

However, in context with gp160 several phenomenons that argue against the use of whole gp160 or gp120 as an immunogen were observed. In vitro experiments showed, that synergism between HIV-1 gp120 and gp120-specific antibodies block human T cell activation (1). This result supports the hypothesis, that also in vivo the humoral immune response against gp120 of HIV-1 suppresses T-cell activation and might be one reason for immunodeficiency. The proposed mechanism for this phenomenon is cross-linking and modulation of CD4 molecules through gp120 and anti-gp120. Experiments from Kion et al.(2) suggest that sequence homologies between gp160 and class II MHC molecules lead to immunodeficiency. In addition, a number of antigenic domains on gp160 are known to induce antibodies that enhance HIV-1 infection (3). Such effects known in context with gp160 could be avoided by using synthetic peptides or other subunit vaccines that only contain immunogenic and neutralizing epitopes as immunogens. Immunogenic peptides corresponding to parts of different viral proteins were already used for successful immunization (4,5,6). The use of synthetic peptides as immunogens offers a number of advantages. The antibodies produced have a predetermined specificity, and in the case of viruses, they can be selected to represent structures on the surface of virions. The synthetic polypeptides also are interesting in that they can induce antibody responses not seen under normal conditions. For example, it was found that in the hemagglutinin of influenza virus there are five major antigenic regions and that under conditions of natural infection the immune response includes antibodies only to these regions. With synthetic polypeptides, an immune response against other regions of the hemagglutinin polypeptide can be generated, and these antibodies have been found to be capable of neutralizing the virus. Therefore it is possible to induce neutralizing antibodies that have a broader reactivity than antibodies induced by whole proteins (4). In addition immunizations with peptides derived from the nucleotide sequence of foot and mouth disease virus (FMDV) are described. In contrast to immunizations with the corresponding whole protein of FMDV, immunizations with these peptides lead to neutralizing antibodies which were also protective (5). Furthermore, a peptide containing part of the V3 loop of gp120 from the HIV-1 isolate HIV-1 IIIb was shown to induce a protective immune response against virus challenge with the same HIV-1 isolate (7,8).

Because synthetic peptides themselves have poor immunogenicity, they have to be coupled to molecules that provide an adjuvant effect such as tetanus toxoid or keyhole limpet hemocyan (5). Another possibility is to clone small peptides as fusion peptides with glutathione S-transferase of *Schistosoma japonicum* (9,10). In addition, attenuated viruses such as vaccinia, polio Sabin type 1 or influenza NA/B-NS can be used as vectors for immunogens. Vaccinia virus is used frequently as a vector of foreign genes of multiple pathogens. For example rabbits inoculated with recombinant vaccinia virus containing sequences from hepatitis B surface antigen (HBsAg), herpes simplex virus glycoprotein D, and influenza virus hemagglutinin produced antibodies to all three foreign antigens (11). Furthermore, a chimeric polio virus that expressed an epitope from gp41 of HIV-1 induced neutralizing antibodies against gp41 in rabbits (12). Since recently it is also possible to change the genome of influenza virus by in vitro mutagenesis (13). By means of this technique it was possible to engineer a stable attenuated influenza A virus (14). In addition by using this technique it was also possible to construct an intertypic chimeric virus, in which a six-amino-acid loop contained in the antigenic site B of the hemagglutinin of an H1 subtype was replaced by the corresponding structures of subtypes H2 and H3 (15). An advantage of influenza virus in this context is the availability of many variants so that repeated vaccination may be possible. Furthermore, influenza virus induces strong secretory and cellular immune responses, which may be advantageous for an anti-HIV-1 vaccine approach. In addition it is unlikely that influenza virus is associated with the development of malignancies. There is no DNA phase involved in the replication of influenza viruses, which excludes the possibility of chromosomal integration of viral influenza genes.

The use of antiidiotypic antibodies is another possibility to achieve a specific immune reaction. Antiidiotypic antibodies are antibodies that specifically recognize and bind the antigen binding site of another antibody. As the combining sites of antibodies can be structurally looked at as a mirror image of the epitope that is bound, an antiidiotypic antibody corresponds to the mirror image of this primary mirror image, which means that an antiidiotypic antibody displays the internal image of the epitope that is bound by the idiotypic antibody. Although one can not always expect to find complete identity between the structure or the amino acid sequence respectively of the antidiotypic antibody with that of the epitope, one can however see effects in practice that allow the conclusion that there is a structural, sequential or functional similarity between antiidiotypic antibodies and the respective epitopes. The use of antiidiotypic antibodies as a vaccine was initially proposed by Nisonoff and Lamoyi (16). In the case of African Sleeping Disease it was first shown that a protective immune response against the causative agent, *Trypanosoma brucei rhodesiense*, could be elicited in BALB/c mice by vacciniating the mice with antiidiotypic antibody (17). In the case of viral antigens, the formation of antiidiotypic antibodies to a neutralizing epitope on the hemagglutinin molecule of Reovirus Type III was investigated. These antiidiotypic antibodies recognized the cellular receptor of Reovirus-hemagglutinin on both, cytolytic T-cells and neuronal cells, and were able to induce in mice a humoral as well as a cellular immune response specific to Reovirus-hemagglutinin (18, 19, 20).

BRIEF DESCRIPTION OF DRAWINGS

FIG. 3*b* shows an antibody titer.

FIG. 3*c* shows neutralization of HIV-1 infection.

DETAILED DESCRIPTION OF THE INVENTION

Figure 1A:
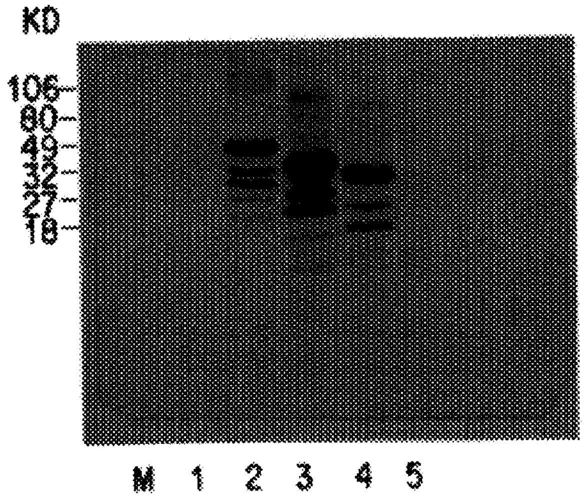
FIGS. 1*a*, 1*b* and 1*c* show Western Blots of Fusion Peptides.
Figure 1B:
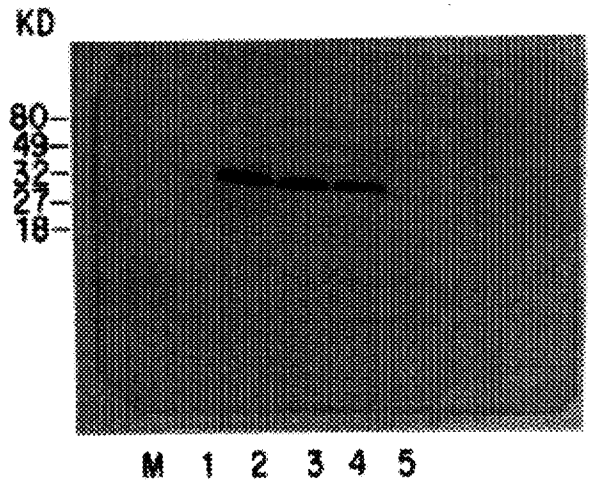
Figure 1C:
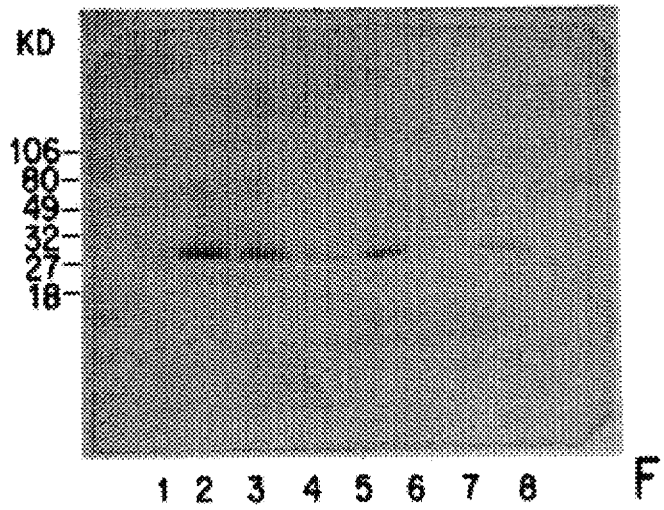
Figure 4:
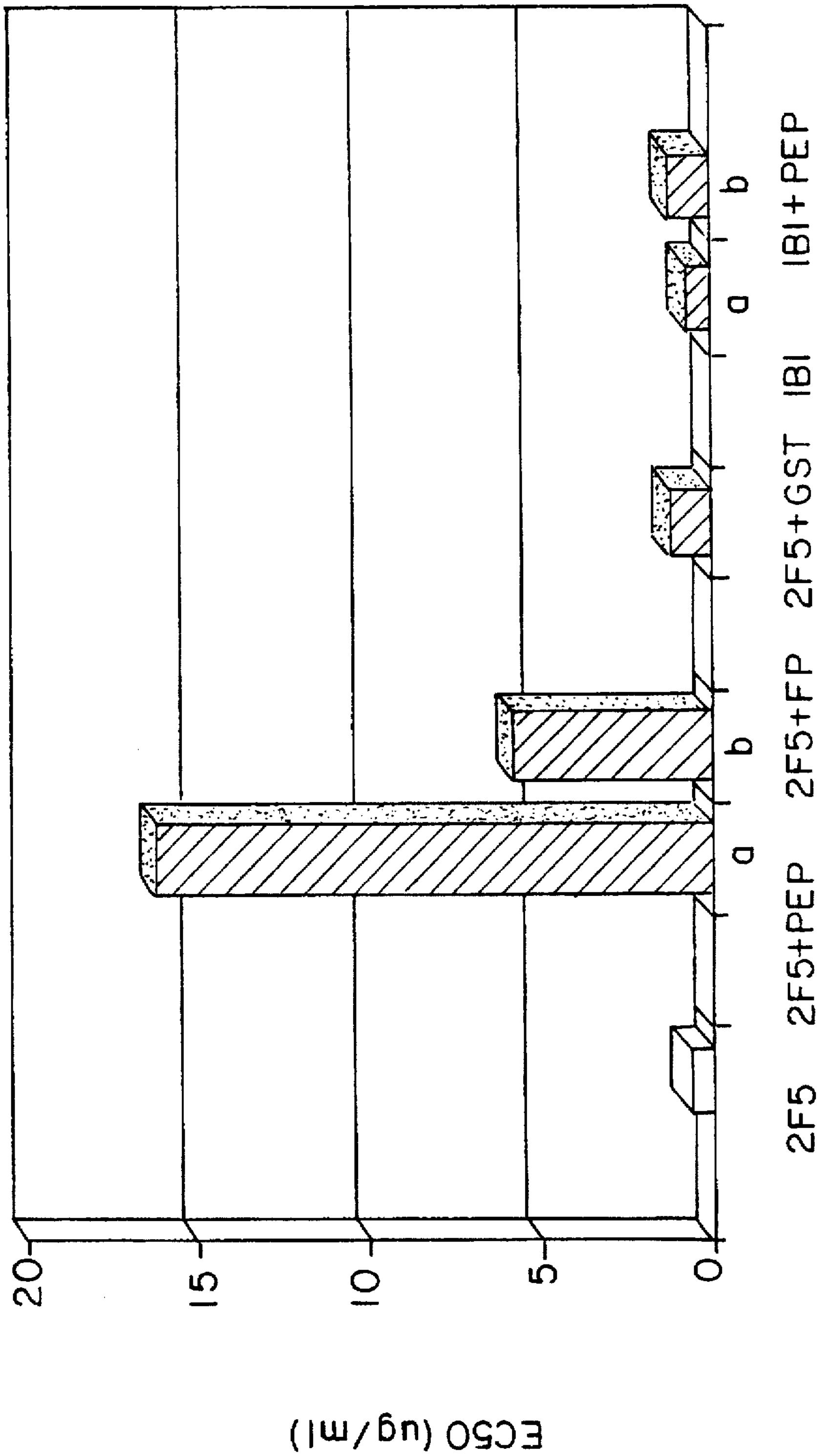
FIG. 4 shows inhibition of neutralization by peptides.

Peptides comprising 6 amino acid residues (aa) that bind specifically to the monoclonal antibody 2F5 were used as immunogens to induce neutralizing antibodies against HIV-1. For identification of these peptides overlapping fragments of gp41 (HIV-1 isolate BH10) were cloned as fusion peptides with glutathiontransferase. The different fusion peptides were obtained through hybridization of gp41 corresponding oligonucleotides which were cloned between the Bam HI and the Eco RI site of the plasmid pGEX-2T (Pharmacia). The recombinant plasmids were transformed into the *E. coli* strain DH5α and expression of the fusion proteins was induced with isopropylthiogalactoside (IPTG). The *E. coli* extract was then purified with glutathion-sepharose 4B columns, loaded on sodiumdodecylsulfate-polyacrylamide gels, separated by electrophoresis and protein expression was analyzed by silver staining. Fusion peptides that were reactive with the monoclonal antibody 2F5 were identified by immunoblotting. Using this method peptides which bind to the monoclonal antibody 2F5 were identified: FIG. 1 shows Western blots of fusion peptides with overlapping fragments of gp160 of HIV-1 (isolate BH10). In contrast to constructs that comprise aa 597 to 677, 634 to 677 and 648 to 677 (the numbering of amino acid residues corresponds to gp160 of HIV-1 isolate BH10, as described in the Swissprot database entry ENV$HIV10) which were reactive with the antibody 2F5, a fusion peptide comprising aa 667 to 677 did not show a positive reaction. This was the first indication that the epitope of the monoclonal antibody 2F5 is formed by aa within the sequence from position 648 to 667 of gp160. Based on these results, overlapping 6-mer peptides of this region were fused with the glutathion S-transferase. As shown in FIG. 1*b* the peptide containing the aminoacid sequence GLU LEU ASP LYS TRP ALA (aa 662–667) SEQ ID NO:1 was highly reactive with the antibody 2F5 whereas for peptides containing the aminoacid sequence LEU ASP LYS TRP ALA SER (aa 663–668) or ASP LYS TRP ALA SER LEU (aa 664–669) reactivity with the monoclonal antibody was significantly lower. A peptide containing amino acid sequence LEU GLU LEU ASP LYS TRP (aa 661–666) showed no reactivity at all. These data suggest that the epitope of the monoclonal antibody comprises the amino acid sequence GLU LEU ASP LYS TRP ALA SEQ ID NO:1 that correspond to aa 662–667 on gp160 of the HIV-1 BH10 isolate. In this context both, a synthetic peptide corresponding to this epitope sequence and a fusion protein containing this sequence were able to inhibit neutralization mediated by the 2F5 antibody (FIG. 4). Sequence comparison of that region revealed that the corresponding aminoacid sequence is highly conserved between otherwise genetically highly divergent HIV-1 isolates (Table 2a). We also were able to show that fusion peptides with aminoacid substitutions—according to different HIV-1 isolates—in this region were also reactive with the 2F5 antibody (FIG. 1*c*).

The presence of antigenic domains around this region has been reported previuosly (21,22). Teeuwsen et al. reported a monoclonal antibody, that reacted with a peptide corresponding to aa 643 to 692 of gp160. In addition Broliden et al. reported that HIV-1 antibody-positive human sera were reactive with a peptide corresponding to region 657–671. However, in both cases a specific epitope was not identified. The monoclonal antibody reported by Teeuwsen et al. had no neutralizing activity. Also the sera reactive with the peptide 657–671 of Broliden et al. showed just partial neutralizing activity. In different neutralization assays this group was able to show neutralizing activity against HIV-1 isolate IIIB but not against SF2 and RF. In contrast to this result the monoclonal antibody 2F5 neutralizes a variety of different HIV-1 isolates including SF2 and RF (table 1). These data suggest that the antibodies of the sera reported by Broliden et al. as well as the monoclonal antibody reported by Teeuwsen et al. have a different specificity and recognize a different epitope than the antibody 2F5.

The application of the peptides described in the present invention as an immunogen has several advantages. They comprise just 6 aa. Thus other gp160 peptide sequences which induce antibodies that enhance HIV-1 infection or lead to immunosuppression can be avoided (2,3). Furthermore an effective HIV-1 vaccine should induce an immune response against HIV-1 isolates that vary considerably in their genomic sequences. In this context sequence comparison in the region of the 2F5 epitope revealed that the epitope of the 2F5 antibody is highly conserved between different HIV-1 isolates (Table 2a). Since peptides with aa substitutions—corresponding to genetically different HIV-1 isolates—were reactive with the 2F5 antibody (FIG. 1*c*), it is likely that antibodies induced by peptides described in the present invention are directed against a variety of divergent HIV-1 isolates. In addition the 2F5 antibody showed neutralizing activity against a wide variety of genetically different HIV-1 isolates which proves that peptides described in the present invention are presented as neutralizing epitopes (Table 1).

In order to know which variations of the epitope sequence are binding to the monoclonal antibody 2F5 we undertook a peptide mapping with a random hexapeptide library displayed on protein III of a filamentous phage (22a). The hexapeptide sequences of the eluted phage particles were compiled (Table 2b).

Figures 2, 3A:
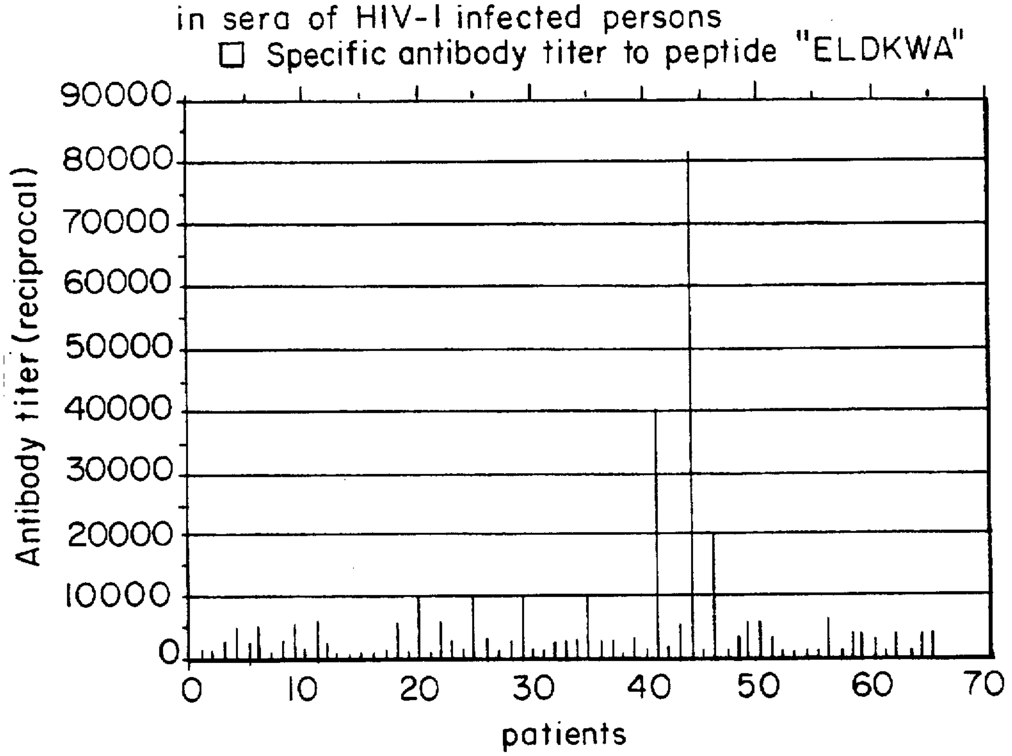
FIG. 2 is a graphic of the specific antibody titers to the peptide with the amino acid sequence "ELDKWA" of 65 sera from HIV-1 positive donors.
FIG. 3*a* shows inhibition of HIV-1 neutralization.

There is a wide range of variation in the progression of HIV-1 related disease in different HIV-1 infected persons. In many cases HIV-1 infection ends up in AIDS-related complex (ARC) and AIDS within some years, while some HIV-1 positive persons remain asymptomatic. It has been shown that antibody-titers against certain peptide epitopes are much lower in AIDS-patients compared to asymptomatic states (23). We found a significant correlation between the antibody-titers to the peptides described in the present invention and HIV-1 related disease progression (FIG. 2). Patients number 20,25,29,35,41,44 and 46 who have a high antibody-titer to peptides described in this invention (FIG. 2), did not show any progression in disease within the last five years so far. This means that generation of antibodies induced by peptides described in the present invention can inhibit or at least reduce the progression of HIV-1 related disease. The fact that there are rarely high antibody-titers to peptides described in this invention found in sera of HIV-1 positive patients indicates that these epitopes on gp160 are not recognized readily by the human immune system, resulting in low HIV-1 neutralizing antibody titers specific to these eptitopes. An objective of the present invention is also to present the peptides described in the invention in a proper form and to induce a sufficient neutralizing immune response.

EXAMPLE 1

The cloning and expression of peptides described in the invention as fusion proteins with glutathion S-transferase (GST) and immunizations of mice with these peptides is described. All cloning methods were done according to standard procedures (24). Oligonucleotides corresponding to the peptides described in the invention were hybridized and cloned between the Bam HI and Eco RI site of the plasmid pGEX-2T (Pharmacia). By this the $NH_2$-terminal ends of these peptides were fused with the COOH-terminal ends of the GST. In addition, a stop codon was added to the COOH-terminal ends of the gp41 peptide sequences. These constructs were transformed into *E. coli* DH5α and expression of the fusion proteins was induced with isopropylthiogalactoside (IPTG). After three hours of induction bacteria were harvested by centrifugation, suspended in phosphate buffered saline (PBS, pH 7.2) containing 1% Triton-X-100 and sonicated. Bacterial debris were spun down by centrifugation and the supernatant was loaded on glutathion-sepharose 4B columns (Pharmacia). Elution of the fusion proteins was done with 20 mM glutathion and 120 mM NaCl in 100 mM Tris-HCl (pH 8.0). Purified fusion proteins obtained with this procedure were used for immunizing mice according to standard procedures. As a control, mice were immunized with GST prepared in the same way as the fusion proteins. Sera from mice taken one week after the last immunization showed high neutralizing titers against peptides described in the invention and inhibited HIV-1 replication in vitro (FIGS. 3*b* and 3*c*).

EXAMPLE 2

Example 2 describes the expression of peptide sequences described in the invention as part of the hemagglutinin of influenza A virus. In vitro mutagenesis was used to introduce this peptide sequence into the antigenic sites A,B,C,D, and E of the hemagglutinin of influenza A virus (25,26).

According to Kohl et al. (27) at page 107 thereof, restriction sites were introduced in the cDNAs by oligonucleotide-directed site-specific mutagenesis (in vitro mutagenesis system, Amersham, UK) at the 5' and 3' ends of the two variable regions as well as a start codon at the 5' end of the heavy chain variable region and a stop codon at the 3' end of the light chain variable region. The domains coding for the variable regions of the antibody were then isolated using the introduced restriction sites and were ligated in the presence of a synthetic double-stranded oligonucleotide according to standard procedures. After this, the engineered gene was cloned and sequenced.

Further, Wiley et al. (26) at pages 375–377 suggested locations for the antigenic sites. An antigenic site is a region of a molecule involved in antibody binding. Although there are no exhaustive immunochemical data such as those used in studies defining the antigenic sites on lysozyme and myoglobin, a combination of the amino acid sequence information and the three-dimensional structure of the 1968 hemagglutinin allows identification of four regions of the Hong Kong hemagglutinin molecule in which amino acid substitutions seem to affect antibody binding.

Site A: An unusual protruding loop from amino acids 140 to 146, which projects 8 Å from the local molecular surface, forms the center of the most obvious antibody-binding site. Clearly the hemagglutinin of each antigenically distinct virus of epidemic significance has a mutation in this region: A/Memphis/102/72: residue 144, Gly to Asp, and residue 122, Thr to Asn; A/Victoria/1/75 and A/Victoria/3/75: residue 145, Ser to Asn, and residue 137, Asn to Ser respectively. Furthermore, the hemagglutinins of a group of monoclonal antibody-selected variants neutralization by single amino acid substitutions in this region: 143, Pro to His, Ser, Thr, Leu; 144, Gly to Asp, and 133, Asn to Lys. Conserved amino acids Gly 134, Ala 138, Cys 139, Phe 147 and Phe (Tyr) 148 occurring at each end of the antigenically variable loop provide the structural foundation of the site in all 10 hemagglutinins examined (including one Avian and one Asian subtype).

Site B: This comprises the external residues 187–196 of an α helix, and adjacent residues along the upper edge of a pocket tentatively implicated in virus receptor binding. Two substitutions in the hemagglutinin of the 1972 virus, A/Memphis/102/72: 188, Asn to Asp, and 155, Thr to Tyr; and two more in that of the 1975 virus, A/Victoria/3/75: 189, Gln to Lys and 193, Ser to Asn characterize the site, but the lack of sequence information for this region of the hemagglutinins of several variants leaves the comparison incomplete. The substitution 186, Ser to Ile in the hemagglutinin of the 30D virus, selected using 'avid-fraction' antisera, may also support the site designation. In addition, the existence of this structure in other hemagglutinins is suggested by the observed conservation of neighboring residues. On the inward face of the helix residues 190 Glu, 191 Gln, 194 Leu and 195 Tyr are conserved in all the known sequences, as are 153 trp and 154 Leu. However, because no amino acid substitutions in the hemagglutinins of variants selected by monoclonal antibodies comparable with those which support the delineation of site A have yet been reported, more direct evidence of antibody binding to this region is not available.

Site C: A bulge in the tertiary structure at the disulfide bond between Cys 52 and Cys 277, 60 Å from the distal tip of the molecule, comprises another antibody-binding site. The hemagglutinins of the viruses from both epidemic periods have substitutions clustered in this region: A/Memphis/102/72: 275, Asp to Gly; A/Victoria/1/75 and Victoria/3/75: 53, Asn to Asp and 278, Ile to Ser respectively. The absence of amino acid sequences for the 275 to 278 region of $HA_1$ from a number of partial sequences may also mean that this list is incomplete. A substitution at position 54, Asn to Lys, in a variant selected by monoclonal antibody prevents its neutralization and variant 30D also fails to react with the same monoclonal antibody. Again the variable amino acids seem to be anchored in a matrix of conserved residues: 50 Lys, 51 Ile (Leu), 52 Cys, 277 Cys, 281 Cys and 286 Gly. The variable residues at all four positions are in direct contact. In the structure of the 1968 hemagglutinin, Asp 275 is hydrogen bonded to Asn 53, Ile 278 is packed against Asn 54, and Cys 52 bonds to Cys 277. Changes in the types of contact between these residues may be the structural alterations to which antibody binding is sensitive.

Site D: In the first three sites, the amino acid substitutions suggested as causing antigenic variation are external and, in principle, directly recognizable by molecules of the immune system. Site D departs from this apparently simple situation (site C may also). Several amino acid substitutions in the hemagglutinins of both natural and laboratory-selected antigenic variants occur in the interface region between subunits in the hemagglutinin trimer: A/Memphis/102/72: 207, Arg to Lys; A/Victoria/3/75: 201, Arg to Lys and 217, Ile to Val; monoclonal variant: 205, Ser to Tyr, and 'avid-fraction' variants 34C : 201, Arg to Gly, and 30D: 220, Arg to Ile. These amino acids may be recognized directly as a result of a relative movement of the globular domains of $HA_1$ to expose the interface regions. However, it is also possible that the actual antibody binding site is remote from these amino acids but affected by the exact fit at the interface, which might be disturbed by the substitutions listed. A site which spans the monomer-monomer boundary or one near the oligosaccharide chain attached at residue 165, which overlaps that boundary, could be particularly sensitive to alterations in the subunit contact region. Residues 242, Val to Ile and 226, Leu to Gln in A/Memphis/102/72; 174, Phe to Ser in A/Victoria/3/75 and 226, Leu to Gln (also near sites A and B) in laboratory variant 29C (refs 15, 16) are likely components of this area. The amino acid sequences of peptides in the 174 and 242 regions are absent from many partial sequences.

The characterization of new variants may provide evidence for additional sites or extend the size of those proposed.

These chimeric DNA-constructs were then "RNP-transfected" into influenza HK/WSN virus (13).

According to Enami (13) at page 3802, the RNA polymerase complex was purified from influenza A/PR/8/34 virus as described by Parvin et al., (1989) *J. Virol.* 63, 5142–5152 and was then used for RNP transfection of MDBK cells. The transfection procedure followed the protocol of Luytjes et al., (1989) *Cell* 59, 1107–1113, except that WSN-HK virus was used as a helper virus at a multiplicity of infection of 1. RNAs used for RNP transfection were obtained by phenol extraction of purified virus or by transcription (using bacteriophage T3 polymerase) of pT3NAv, pT3NAv mut1, and pT3NAv mut2. All plasmids were digested with Ksp6321, end-filled by Klenow enzyme (BRL), and then transcribed in a runoff reaction.

These chimeric influenza/HIV viruses had the antigenic properties of said peptide. In antibody-adsorption experiments these chimeric viruses inhibited HIV-1 neutralization through the antibody 2F5 (FIG. 3*a*). Antisera of mice immunized with the chimeric viruses were reactive with said peptides (FIG. 3*b*). Furthermore, in vitro these antisera neutralized different HIV-1 isolates (FIG. 3*c*).

EXAMPLE 3

Example 3 describes the expression of peptides described in the invention as part of a so called "immunological supermolecule", in where the peptide sequence is inserted into the linker which connects the variable regions of the heavy and light chain of an immunoglobulin molecule. Specifically a single chain Fv construct of a neutralizing anti-HIV-gp120 antibody was made according to standard procedures (27) (i.e. see discussion of Kohl et al. in Example 1). In this construct peptide sequences described in the invention were inserted into the linker which connects the variable region of the light chain with the variable region of the heavy chain. This recombinant protein was expressed in *E. coli* and purified according to standard procedures. Two functions were observed with this construct. First this construct showed the antigen binding properties of the original antibody and in addition this construct induced, when injected into mice, antibodies that neutralized different HIV-1 isolates (FIG. 3*c*).

This "immunological supermolecule" provides the possibility to obtain an active and passive immunization at the same time. Basically in such a construct the antigen binding neutralizing properties of an antibody and the presentation of a neutralizing epitope are combined. In already HIV-1 infected persons the progression of infection could be slowed down with the first application by the antigen binding neutralizing properties, before the effective onset of the immune system is triggered by the neutralizing epitopes of this molecule. Thus the usual observed "time lag" between immunization and effective immune response of a typical active immunization could be overcome. In addition it is most likely that during neutralization of already present HIV-1 virions the presentation of the epitope is very efficient.

EXAMPLE 4

Example 4 describes the formation of antiidiotypic antibodies to antibody 2F5 as well as the production of an antiidiotypic antibody by means of in vitro recombination techniques.

Antibody 2F5 was used to immunize mice in order to induce the formation of antiidiotypic antibody. The immunization scheme used was according to standard procedures in order to enhance the frequency at which antiidiotypic antibodies are developed in the animal. The polyclonal sera such obtained were tested for their immunoreactivity, whereby it was determined by means of antigen-competition ELISA that a part of the humoral immune response was indeed directed against the combining site of the antibody 2F5. Thus it was proven that in those sera antiidiotypic antibodies where present. In order to test the concept of vaccination by means of antiidiotypic antibodies, the sera containing antiidiotypic antibodies where subsequently used to immunize another group of mice. After completion of this immunization procedure, it was possible to detect an immune response to the antiidiotypic sera that was qualitatively comparable to the above described immune reaction against the HIV-1 peptide-part of the glutathion-S-transferase fusion protein as described in example 1.

Since it was now proven, that the described peptide has the quality necessary to act as an immunogen, and since furthermore it had been shown that by using antiidiotypic antibodies with internal image quality of the described peptide it was possible to induce a HIV-1 neutralizing immune response, an antiidiotypic antibody was constructed by means of in vitro recombination techniques. In order to achieve this goal, one or more hypervariable regions (or parts thereof) of an existing, molecularly cloned antibody where substituted by peptide sequences described in the invention. The respective constructs where expressed as single chain Fv fragments in *E. coli*, and the recombinant proteins where purified according to standard methods. Immunization of mice with the antiidiotypic proteins such produced lead to a HIV-1 neutralising immune response (FIG. 3*c*).

EXAMPLE 5

Example 5 describes the peptide mapping with a random hexapeptide library and immunizations of mice with phages containing peptides according to SEQ ID NO: 10 through SEQ ID NO: 25. The monoclonal antibody 2F5 was coated onto polystyrol tubes (Maxisorp, Nunc, Denmark) at a concentration of 5 ug/ml in coating buffer (0.1M Na-Carbonate buffer, pH 9.6) overnight at 4° C. After washing with PBS, the surface was blocked with PBS containing 5%w/v skimmed milk powder at 36° C. for 2 hours. Washing with PBS was followed by incubation of a hexapeptide phage display library ($10^{11}$ transduction units in TPBS (PBS including 0.5% v/v Tween 20) overnight at 5° C. Extensive washing with TPBS was followed by elution of phage with elution buffer (0.1N HCl/Glycine pH 2.2, 1 mg BSA/ml). The eluate is neutralized with 1M Tris and used for infection of *E. coli* K91Kan. Phage is prepared from the infected culture by the methods described (22a).

According to Scott et al. (22a) at page 389, phage for sequencing and ELISA were propagated in NZY-Tc medium and partially purified by two precipitations with polyethylene glycol (PEG) and one precipitation in acid. After cells were removed by centrifugation, phage from 1.8 ml of supernatant were precipitated twice with PEG; all the supernatant was removed and the redissolved precipitate from the first precipitation was centrifuged for 1 minute in a microfuge before reprecipitation from the supernatant. Phage from the second PEG precipitation were dissolved in 210 µl of 0.15M NaCl, microfuged for 1 minute, precipitated from 200 µl of the supernatant by adding 21.2 µof 1M acetic acid, and incubated for 10 minutes at room temperature (~21° C.) and 10 minutes on ice [W. Wickner, *Proc. Natl. Acad. Sci. U.S.A.* 72, 4749 (1975)]. Phage were sedimented (microfuge, 45 minutes, 4° C., with removal of all supernatant) and dissolved in 62 µl of TBS. Phage concentrations were ~$10^{10}$ particles per microliter as determined by gel electrophoresis of viral DNA.

The procedure is repeated 3 times. The final eluate was used to produce transduced *E. coli* K91Kan. DNA of these clones was sequenced and the respective phage displayed hexapeptide sequence was derived by computer translation.

Clones with the SEQ ID NO:10 through 25 (Table 2) were used for phage preparation and the respective phages were injected into mice. After two booster injections the respective sera were tested for HIV-1 neutralizing activity. All of these sera were neutralizing in vitro. The control serum was produced by immunization with wild-type phage f1 and did not neutralize HIV-1. In addition, oligonucleotides coding for SEQ ID NO: 10 through 25 were introduced into gene VIII of fd-tet between aa 27 and 28 of the unmature protein VIII by standard cloning techniques. The recombinant phages were produced in *E. coli* K91Kan, purified by standard techniques (PEG mediated precipitation followed by CsCl gradient centrifugation) and used as immunogen. The respective sera were found to be neutralizing in HIV-1 neutralizing assays whereas anti-wild type fd-tet was not.

LITERATURE

1. Mittler, R. S., and K. Hoffmann. 1989. Synergism between HIV GP120 and gp 120-specific antibody in blocking human T cell activation, Science 245: 1380–1382
2. Kion, T. A., and G. W. Hoffmann. 1991. Anti-HIV and anti-anti-MHC antibodies in alloimmune and autoimmune mice, Science 253: 1138–1140
3. Jiang S., K. Lin and A. R. Neurath. 1991. Enhancement of human immunodefeciency virus type 1 infection by antisera to peptides from the envelope glycoproteins gp120/gp41, J. Exp. Med. USA 174: 1557–1563
4. Green, N., H. Alexander, A. Olson, S. Alexander, T. M. Shinnck, J. G. Sutciffle, and R. A. Lerner. 1982. Immunogenic Structure of the Influenza Virus Hemagglutinin, Cell 28: 477–487
5. Bittle, J. L., R. A. Houghten, H. Alexander, T. M. Shinnick, J. G. Sutciffle and R. A. Lerner. 1982. Protection against Foot-and-mouth disease by immunization with a chemically synthesized peptide predicted from the viral nucleotide sequence, Nature 298: 30–33
6. R. A. Lerner. 1982. Tapping the immunological repertoire to produce antibodies of predetermined specificity, Nature 299: 592–596
7. Wahren, B., G. Bratt, J. Hinkula, G. Gilljam, S. Nordlund, P. A. Broliden, L. Akerblom, B. Morein, and E. Sandstr öm. 1990. Monoclonal antibodies given as passive treatment to HIV-infected individuals, Cinquieme Colloque des Cent Gardes: 263–268
8. Emini, E. A., W. A. Schleif, J. H. Nunberg, A. J. Conley, Y. Eda, S. Tokiyoshi, S. D. Putney, S. Matsushita, K. E. Cobb, C. M. Jett, J. W. Eichberg, and K. K. Murthy. 1992. Prevention of HIV-1 infection in chimpanzees by gp 120 V3 domain- specific monoclonal antibody, Nature 355: 728–730
9. Fikrig E., S. W. Barthold, F. S. Kantor,, and R. A. Flavell. 1990. Protection of mice against the lyme disease agent by immunizing with recombinant OspA, Science 250: 553–556
10. Johnson K. S., G. B. L. Harrison, M. W. Lightowlers, K. L. O'Hoy, W. G. Cougle, R. P. Dempster, S. B. Lawrence, J. G. Vinton, D. D. Heath, and M. D. Rickard. 1989. Vaccination against ovine cysticercosis using a defined recombinant antigen, Nature 338: 585–587.
11. Perkus, M. E., A. Piccini, R. R. Lipinskas, and E. Paoletti. 1985. Recombinant vaccinia virus:Immunization against multiple pathogens, Science 229: 981–984
12. Evans J. D., J. McKeating, J. M. Meredith, K. L. Burke, K. Katrak,l A. John, M. Ferguson, P. D. Minor, R. A. Weiss, and J. W. Almond. 1989. An engineered Poliovirus chimaera elicits broadly reactive HIV-1 neutralizing antibodies, Nature 339: 385–388.
13. Enami M., W. Luytjes, M. Krystal, and P. Palese et al. 1990. Introduction of site-specific mutations into the genome of Influenza virus, Proc. Natl. Acad. Sci. USA 87: 3802–3805.
14. Muster T., E. K. Subbarao, M. Enami, B. R. Murphy, and P. Palese. 1991. An Influenza A virus containing Influenza B virus 5' and 3' noncoding regions on the neuraminidase gene is attenuated in mice, Proc. Natl. Acad. Sci. USA 88: 5177–5181.
15. Li, S, J. L. Schulmann, T. Moran, C. Bona, and P. Palese. 1992. Influenza-A virus transfectants with chimeric Hemagglutinins containing epitopes from different subtypes, J. Virol. 66.: 399–404
16. Nisonoff A., E. Lamoyi. 1981. Clin. Immunol. Immunopathol. 21: 397
17. Sacks D. L., K. M. Esser and A. Sher. 1982. J. Exp. Med. 155: 1108
18. Kauffman R. S., J. H. Noseworthy, J. T. Nepom, R. Finberg, B. N. Fields, and M. I. Greene. 1983. J. Immunol. 131: 2539
19. Sharpe A. H., G. N. Gaulton, K. K. McDade, B. N. Fields, and M. I. Greene. 1984. J. Exp. Med. 160: 1195
20. Gaulton G. N., and M. I. Greene. 1986. Ann. Rev. Immunol. 4: 253
21. Broliden, P., A. Gegerfelt, P. Clapham, J. Rosen, E. Feny ö, B. Wahren, and K. Broliden. 1992. Identification of human neutralizing regions of the human immunodeficiency virus type-1 envelope glycoproteins, Proc. Natl. Acad. Sci. USA 89/2:461–465.

22. Teeuwsen V. J., K. H. Siebelnik, S. Crush-Stanton, A. D. B. Swerdlow, J. J. Schalken, J. Goudsmit, R. Van De Akker, M. J. Stukart, F. G. Uytdehaag, and A. D. Osterhaus. 1990. Production and characterization of a human monoclonal antibody, reactive with conserved epitope on gp41 of human immunodeficiency virus type 1, AIDS Res Hum Retroviruses 6: 381–392.

22a. Scott, J. K. and G. P. Smith. 1990. Searching for peptide ligands with an epitope library, Science 249: 386–390

23. Neurath, A. R., N. Strick, P. Taylor, P. Rubinstein, and C. E. Stevens. 1990. Search for epitope- specific antibody responses to the human immunodeficiency virus (HIV-1) envelope glycoproteins signifying resistance to desease development, AIDS Res Hum Retroviruses 6: 1183–1191

24. Sambrook, J., E. F. Fritsch and T. Maniatis. 1989. Molecular Cloning. A Laboratory manual. Cold Spring Harbor Laboratory Press, New York 25. Wharton, S. A., W. Weis, J. J. Shekel, and D. C. Wiley. 1989. Strucutre, function and antigenicity of the Hemagglutinin of Influenza virus, in: R. M. Krug (ed), The Influenza Viruses, Plenum Press, New York 26. Wiley, D. C., I. A. Wilson and J. J. Shekel. 1981. Structural identification of the antibody binding sites of Hong Kong Influenza Hemagglutinin and their involvement in the antigenic variation, Nature 289: 373–378

27. Kohl, J., F. Rüker, G. Himmler, E. Razazzi, and H. Katinger. 1991. Cloning and expression of a HIV-1 specific single-chain Fv region fused to *Escherichia coli* Alkaline Phosphatase, Ann. New York Acad. Sci. 646: 106–114

TABLES

| | Isolate | | | | | |
|---|---|---|---|---|---|---|
| | IIIB | MN | RF | SF2 | A | C |
| a) in vitro neutralization assays: | | | | | | |
| number of positive tests | 8/8 | 2/2 | 2/2 | n.t. | 8/8 | 4/4 |
| neutralizing concentration (Íg/ml) | 10 | 10 | 10 | 50 | 10 | |
| b) syncitia inhibition assay: | | | | | | |
| number of positive tests | 18/18 | 11/11 | 6/10 | 1/1 | 1/1 | 2/3 |
| $EC_{50}$ (Íg/ml) | 12,8 | 12 | 13,7 | 1,9 | 27 | 10 |

TABLE 1

Neutralizing Properties of Human Monoclonal Antibody 2F5 a) in vitro neutralization assay: Different concentrations of the 2F5 antibody were incubated with cellfree virus preparations ($10^2$–$10^3$ $TCID_{50}$) 1 h at 37° C. Aliquots of $10^5$ H9 cells were added to virus/antibody mixtures and incubated for an additional hour at 37° C. After 20 days p24 antigen concentration as indicator for virus replication was determined from supernatants according to standard procedures.

b) Syncytia inhibition assay: Antibody/virus mixtures were prepared as described in table 1a. To this mixtures $10^5$ AA2 cells were added and incubated at 37° C. After 5 days syncitia formation as indicator for HIV-1 replication was evaluated. Abbrevations:A and C are clinical isolates from Vienna

| | | | | | | | | | |
|---|---|---|---|---|---|---|---|---|---|
| E | L | D | K | W | A | | SEQ ID NO: 1 | 43 | a) |
| A | : | : | : | : | : | | SEQ ID NO: 4 | 5 | |
| : | : | N | : | : | : | | SEQ ID NO: 2 | 1 | |
| : | : | : | : | : | D | | SEQ ID NO: 3 | 2 | |
| A | : | : | T: | : | | SEQ ID NO: 8 | 3 | | |
| Q | : | : | : | : | : | | SEQ ID NO: 6 | 2 | |
| : | : | : | T | : | : | | SEQ ID NO: 7 | 1 | |
| G | : | : | : | : | : | | SEQ ID NO: 5 | 1 | |
| K | : | : | E | : | : | | SEQ ID NO: 9 | 1 | |
| — | — | — | — | — | — | — | SEQ ID NO: | | |
| S | : | : | : | : | : | SEQ ID NO: 10 | SEQ ID NO: | | |
| G | R | : | : | : | : | SEQ ID NO: 11 | SEQ ID NO: | | |
| G | A | : | : | : | : | SEQ ID NO: 12 | SEQ ID NO: | | |
| A | H | E | : | : | : | SEQ ID NO: 13 | SEQ ID NO: | | |
| A | C | : | Q | : | : | SEQ ID NO: 14 | | | |
| G | A | : | : | : | G | SEQ ID NO: 15 | | | |
| G | A | : | : | : | N | SEQ ID NO: 16 | | | |
| G | A | : | : | : | C | SEQ ID NO: 17 | | | |
| G | A | : | : | : | V | SEQ ID NO: 18 | | | |
| G | A | : | : | : | H | SEQ ID NO: 19 | | | |
| G | A | : | : | C | H | SEQ ID NO: 20 | | | |
| G | A | : | : | C | Q | SEQ ID NO: 21 | | | |
| A | Y | : | : | : | S | SEQ ID NO: 22 | | | |
| A | F | : | : | : | V | SEQ ID NO: 23 | | | |
| G | P | : | : | : | G | SEQ ID NO: 24 | | | |
| A | R | : | : | : | A | SEQ ID NO: 25 | | | |

TABLE 2

Peptide sequences bound by antibody 2F5 a: sequences present on gp160 of different HIV-1 isolates. The number on the right side of each sequence indicates the number of incidences in the databases that were screened (SwissProt and GenPept).

b: binding sequences found by screening a random hexapeptide library expressed on the surface of filamentous phage (sequences already described in a) are not included).

We claim:

1. A peptide consisting of an amino acid sequence selected from the group consisting of SEQ ID NO: 1 through SEQ ID No. 25.

2. The peptide according to claim 1, bound to an adjuvant through chemical interaction.

3. The peptide according to claim 1, having the sequence of SEQ ID NO. 1.

4. The peptide according to claim 2, having the sequence of SEQ ID NO: 1.

5. The peptide according to claim 1, which is genetically encoded by a nucleotide sequence selected from the group consisting of SEQ ID NO: 26 through SEQ ID NO: 50, respectively, or by a nucleotide sequence equivalent thereto due to the degeneracy of the genetic code.

6. The peptide according to claim 2, wherein said adjuvant is selected from the group consisting of an antibody, an antibody fragment, a virus, a part of a virus, a phage and glutathione S-transferase.

7. The peptide according to claim 6, having the sequence of SEQ ID No. 1.

8. The peptide according to claim 6, wherein the adjuvant is an antibody.

9. The peptide according to claim 6, wherein the adjuvant is an antibody fragment.

10. The peptide according to claim 6, wherein the adjuvant is a virus.

11. The peptide according to claim 6, wherein the adjuvant is part of a virus.

12. The peptide according to claim 6, wherein the adjuvant is a phage.

13. The peptide according to claim 6, wherein the adjuvant is glutathione S-transferase.

* * * * *

SEQUENCE LISTING ( 1 ) GENERAL INFORMATION:

( i i i ) NUMBER OF SEQUENCES: 50

( 2 ) INFORMATION FOR SEQ ID NO: 1:

( i ) SEQUENCE CHARACTERISTICS:

( A ) LENGTH: 6
( B ) TYPE: AMINO ACID
( C ) STRANDEDNESS: SINGLE
( D ) TOPOLOGY: UNKNOWN ( i i ) MOLECULE TYPE:
( A ) DESCRIPTION: PEPTIDE ( i i i ) HYPOTHETICAL: No ( v i ) ORIGINAL SOURCE:
( A ) ORGANISM: HIV-1
( B ) STRAIN:
( C ) INDIVIDUAL ISOLATE: BH10
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: GP160 FRAGMENT
( B ) LOCATION: RESIDUE 662 TO 667
( C ) IDENTIFICATION METHOD:
( D ) OTHER INFORMATION: EPITOPE OF HUMAN MONCLONAL ANTIBODY DIRECTED AGAINST HIV-1 GP160

( x i ) SEQUENCE DESCRIPTION: SEQ ID NO: 1:

Glu Leu Asp Lys Trp Ala 6
1 5

( 2 ) INFORMATION FOR SEQ ID NO: 2:

( i ) SEQUENCE CHARACTERISTICS:
( A ) LENGTH: 6
( B ) TYPE: AMINO ACID
( C ) STRANDEDNESS: SINGLE
( D ) TOPOLOGY: UNKNOWN ( i i ) MOLECULE TYPE: PEPTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: JS4/26
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:GP160 FRAGMENT
( B ) LOCATION: RESIDUE 655 TO 660
( C ) IDENTIFICATION METHOD:
( D ) OTHER INFORMATION: EPITOPE OF A HUMAN MONOCLONAL ANTIBODY DIRECTED AGAINST HIV-1 GP160.

( x i ) SEQUENCE DESCRIPTION: SEQ ID NO: 2:

Glu Leu Asn Lys Trp Ala 6
1 5

( 2 ) INFORMATION FOR SEQ ID NO: 3:

( i ) SEQUENCE CHARACTERISTICS:
( A ) LENGTH: 6
( B ) TYPE: AMINO ACIDS
( C ) STRANDEDNESS: SINGLE
( D ) TOPOLOGY: UNKNOWN ( i i ) MOLECULE TYPE: PEPTIDE

-continued ( i i i ) HYPOTHETICAL: No ( i v ) ORIGINAL SOURCE:
( A ) ORGANISM: HIV-1
( B ) STRAIN:
( C ) INDIVIDUAL ISOLATE: PATIENT 3L
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: GP160 FRAGMENT
( B ) LOCATION: RESIDUE 164 TO 169
( C ) IDENTIFICATION METHOD:
( D ) OTHER INFORMATION: EPITOPE OF A HUMAN MONOCLONAL ANTIBODY DIRECTED AGAINST HIV-1 GP160

( x i ) SEQUENCE DESCRIPTION: SEQ ID NO: 3:

Glu Leu Asp Lys Trp Asp 6
1 5

( 2 ) INFORMATION FOR SEQ ID NO: 4:

( i ) SEQUENCE CHARACTERISTICS:
( A ) LENGTH: 6
( B ) TYPE: AMINO ACID
( C ) STRANDEDNESS: SINGLE
( D ) TOPOLOGY: UNKNOWN ( i i ) MOLECULE TYPE: PEPTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: SF170
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: GP160 FRAGMENT
( B ) LOCATION: RESIDUE 667 TO 672
( C ) IDENTIFICATION METHOD:
( D ) OTHER INFORMATION: EPITOPE OF A HUMAN MONOCLONAL ANTIBODY DIRECTED AGAINST HIV-1 GP160

( x i ) SEQUENCE DESCRIPTION: SEQ ID NO: 4:

Ala Leu Asp Lys Trp Ala 6
1 5

( 2 ) INFORMATION FOR SEQ ID NO: 5:

( i ) SEQUENCE CHARACTERISTICS:
( A ) LENGTH: 6
( B ) TYPE: AMINO ACID
( C ) STRANDEDNESS: SINGLE
( D ) TOPOLOGY: UNKNOWN ( i i ) MOLECULE TYPE: PEPTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: JH3
( D ) DEVELOPMENTAL STAGE:
( E ) HAPLOTYPE:

-continued ( F ) TISSUE TYPE:
( G ) CELL TYPE:
( H ) CELL LINE:
( I ) ORGANELLE:

( i x ) FEATURE:
( A ) NAME/KEY: GP160 FRAGMENT
( B ) LOCATION: RESIDUE 673 TO 678
( C ) IDENTIFICATION METHOD:
( D ) OTHER INFORMATION: EPITOPE OF A HUMAN MONOCLONAL ANTIBODY DIRECTED AGAINST HIV-1 GP160

( x i ) SEQUENCE DESCRIPTION: SEQ ID NO: 5:

Gly Leu Asp Lys Trp Ala 6
1 5

( 2 ) INFORMATION FOR SEQ ID NO: 6:

( i ) SEQUENCE CHARACTERISTICS:
( A ) LENGTH: 6
( B ) TYPE: AMINO ACID
( C ) STRANDEDNESS: SINGLE
( D ) TOPOLOGY: UNKNOWN ( i i ) MOLECULE TYPE: PEPTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: Z-84
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: GP160 FRAGMENT
( B ) LOCATION: RESIDUE 669 TO 674
( C ) IDENTIFICATION METHOD:
( D ) OTHER INFORMATION: EPITOPE OF A HUMAN MONOCLONAL ANTIBODY DIRECTED AGAINST HIV-1 GP160

( x i ) SEQUENCE DESCRIPTION: SEQ ID NO: 6:

Gln Leu Asp Lys Trp Ala 6
1 6

( 2 ) INFORMATION FOR SEQ ID NO: 7:

( i ) SEQUENCE CHARACTERISTICS:
( A ) LENGTH: 6
( B ) TYPE: AMINO ACID
( C ) STRANDEDNESS: SINGLE
( D ) TOPOLOGY: UNKNOWN ( i i ) MOLECULE TYPE: PEPTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: CAM1 PROVIRAL GENOME
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: GP160 FRAGMENT
( B ) LOCATION: RESIDUE 662 TO 667

-continued ( C ) IDENTIFICATION METHOD:
( D ) OTHER INFORMATION: EPITOPE OF A HUMAN MONOCLONAL ANTIBODY DIRECTED AGAINST HIV-1 GP160

( x i ) SEQUENCE DESCRIPTION: SEQ ID NO: 7:

```
Glu Leu Asp Thr Trp Ala                                        6
1               5
```

( 2 ) INFORMATION FOR SEQ ID NO: 8:

( i ) SEQUENCE CHARACTERISTICS:
( A ) LENGTH: 6
( B ) TYPE: AMINO ACID
( C ) STRANDEDNESS: SINGLE
( D ) TOPOLOGY: UNKNOWN ( i i ) MOLECULE TYPE: PEPTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: JS4/6
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: GP160 FRAGMENT
( B ) LOCATION: RESIDUE 659 TO 664
( C ) IDENTIFICATION METHOD:
( D ) OTHER INFORMATION: EPITOPE OF A HUMAN MONOCLONAL ANTIBODY DIRECTED AGAINST HIV-1 GP160

( x i ) SEQUENCE DESCRIPTION: SEQ ID NO: 8:

```
Ala Leu Asp Thr Trp Ala                                        6
1               5
```

( 2 ) INFORMATION FOR SEQ ID NO: 9:

( i ) SEQUENCE CHARACTERISTICS:
( A ) LENGTH: 6
( B ) TYPE: AMINO ACID
( C ) STRANDEDNESS: SINGLE
( D ) TOPOLOGY: UNKNOWN ( i i ) MOLECULE TYPE: PEPTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: SBB
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: GP160 FRAGMENT
( B ) LOCATION: RESIDUE 413 TO 418
( C ) IDENTIFICATION METHOD:
( D ) OTHER INFORMATION: EPITOPE OF A HUMAN MONOCLONAL ANTIBODY DIRECTED AGAINST HIV-1 GP160

( x i ) SEQUENCE DESCRIPTION: SEQ ID NO: 9:

```
Lys Leu Asp Glu Trp Ala                                        6
1               5
```

-continued ( 2 ) INFORMATION FOR SEQ ID NO: 10:

( i ) SEQUENCE CHARACTERISTICS:
( A ) LENGTH: 6
( B ) TYPE: AMINO ACID
( C ) STRANDEDNESS: SINGLE
( D ) TOPOLOGY: UNKNOWN ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 10:

Ser Leu Asp Lys Trp Ala 6
1 5

( 2 ) INFORMATION FOR SEQ ID NO: 11:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 11:

Gly Arg Asp Lys Trp Ala 6
1 5

( 2 ) INFORMATION FOR SEQ ID NO: 12:

( i ) SEQUENCE CHARACTERISTICS:
( A ) LENGTH: 6
( B ) TYPE: AMINO ACID
( C ) STRANDEDNESS: SINGLE

-continued ( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 12:

Gly Ala Asp Lys Trp Ala 6
1 5

( 2 ) INFORMATION FOR SEQ ID NO: 13:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 13:

Ala His Glu Lys Trp Ala 6
1 5

( 2 ) INFORMATION FOR SEQ ID NO: 14:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5

-continued ( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 14:

Ala Cys Asp Gln Trp Ala 6
1 5

( 2 ) INFORMATION FOR SEQ ID NO: 15:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 15:

Gly Ala Asp Lys Trp Gly 6
1 5

( 2 ) INFORMATION FOR SEQ ID NO: 16:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

(ix) FEATURE:
(A) NAME/KEY: p3 FUSION PROTEIN FRAGMENT
(B) LOCATION: RESIDUE 4 TO 9
(C) IDENTIFICATION METHOD:
(D) OTHER INFORMATION: HEXAPEPTIDE FROM A RANDOM LIBRARY SCREENING AND ITS BINDING TO MONCLONAL ANTIBODY 2F5

(xi) SEQUENCE DESCRIPTION: SEQ ID NO: 16:

Gly Ala Asp Lys Trp Asn 6
1 5

(2) INFORMATION FOR SEQ ID NO: 17:

(i) SEQUENCE CHARACTERISTICS:
(A) LENGTH: 6
(B) TYPE: AMINO ACID
(C) STRANDEDNESS: SINGLE
(D) TOPOLOGY: Unknown (ii) MOLECULE TYPE: PEPTIDE (iii) HYPOTHETICAL: No (iv) ORIGINAL SOURCE:
(A) ORGANISM: FILAMENTOUS PHAGE fUSE5
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: p3 FUSION PROTEIN FRAGMENT
(B) LOCATION: RESIDUE 4 TO 9
(C) IDENTIFICATION METHOD:
(D) OTHER INFORMATION: HEXAPEPTIDE FROM A RANDOM LIBRARY SCREENING AND ITS BINDING TO MONCLONAL ANTIBODY 2F5

(xi) SEQUENCE DESCRIPTION: SEQ ID NO: 17:

Gly Ala Asp Lys Trp Cys 6
1 5

(2) INFORMATION FOR SEQ ID NO: 18:

(i) SEQUENCE CHARACTERISTICS:
(A) LENGTH: 6
(B) TYPE: AMINO ACID
(C) STRANDEDNESS: SINGLE
(D) TOPOLOGY: Unknown (ii) MOLECULE TYPE: PEPTIDE (iii) HYPOTHETICAL: No (iv) ORIGINAL SOURCE:
(A) ORGANISM: FILAMENTOUS PHAGE fUSE5
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: p3 FUSION PROTEIN FRAGMENT
(B) LOCATION: RESIDUE 4 TO 9
(C) IDENTIFICATION METHOD:
(D) OTHER INFORMATION: HEXAPEPTIDE FROM A RANDOM LIBRARY SCREENING AND ITS BINDING TO MONCLONAL ANTIBODY 2F5

-continued ( x i ) SEQUENCE DESCRIPTION: SEQ ID NO: 18:

Gly Ala Asp Lys Trp Val 6
1 5

( 2 ) INFORMATION FOR SEQ ID NO: 19:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 19:

Gly Ala Asp Lys Trp His 6
1 5

( 2 ) INFORMATION FOR SEQ ID NO: 20:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 20:

Gly Ala Asp Lys Cys His 6
1 5

( 2 ) INFORMATION FOR SEQ ID NO: 21:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 21:

Gly Ala Asp Lys Cys Gln 6
1 5

( 2 ) INFORMATION FOR SEQ ID NO: 22:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 22:

Ala Tyr Asp Lys Trp Ser 6
1 5

( 2 ) INFORMATION FOR SEQ ID NO: 23:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE -continued ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 23:

Ala Phe Asp Lys Trp Val 6
1 5

( 2 ) INFORMATION FOR SEQ ID NO: 24:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 24:

Gly Pro Asp Lys Trp Gly 6
1 5

( 2 ) INFORMATION FOR SEQ ID NO: 25:

( i ) SEQUENCE CHARACTERISTICS:
( A ) LENGTH: 6
( B ) TYPE: AMINO ACID
( C ) STRANDEDNESS: SINGLE
( D ) TOPOLOGY: Unknown ( i i ) MOLECULE TYPE: PEPTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:

-continued ( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN FRAGMENT
( B ) LOCATION: RESIDUE 4 TO 9
( C ) IDENTIFICATION METHOD:
( D ) OTHER INFORMATION: HEXAPEPTIDE FROM A RANDOM LIBRARY SCREENING AND ITS BINDING TO MONCLONAL ANTIBODY 2F5

( x i ) SEQUENCE DESCRIPTION: SEQ ID NO: 25:

Ala Arg Asp Lys Trp Ala 6
1 5

( 2 ) INFORMATION FOR SEQ ID NO: 26:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: BH10
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: SEQUENCE FROM GP160

( x i ) SEQUENCE DESCRIPTION: SEQ ID NO: 26:

GAATTAGATA AATGGGCA 18

( 2 ) INFORMATION FOR SEQ ID NO: 27:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: JS4/26
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: SEQUENCE FROM GP160

-continued ( x i ) SEQUENCE DESCRIPTION: SEQ ID NO: 27:

GAATTGAATA AGTGGGCA 18

( 2 ) INFORMATION FOR SEQ ID NO: 28:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: PATIENT 3L
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: SEQUENCE FROM GP160

( x i ) SEQUENCE DESCRIPTION: SEQ ID NO: 28:

GAATTAGATA AGTGGGAC 18

( 2 ) INFORMATION FOR SEQ ID NO: 29:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: SF170
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: SEQUENCE FROM GP160

( x i ) SEQUENCE DESCRIPTION: SEQ ID NO: 29:

GCATTGGACA AGTGGGCA 18

( 2 ) INFORMATION FOR SEQ ID NO: 30:

( i ) SEQUENCE CHARACTERISTICS:
( A ) LENGTH: 18
( B ) TYPE: NUCLEIC ACID
( C ) STRANDEDNESS: SINGLE

-continued ( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: JH3
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: SEQUENCE FROM GP160

( x i ) SEQUENCE DESCRIPTION: SEQ ID NO: 30:

GGGTTAGATA AATGGGCA 18

( 2 ) INFORMATION FOR SEQ ID NO: 31:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: Z-84
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: SEQUENCE FROM GP160

( x i ) SEQUENCE DESCRIPTION: SEQ ID NO: 31:

CAATTGGACA AATGGGCA 18

( 2 ) INFORMATION FOR SEQ ID NO: 32:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE:CAM1 PROVIRAL GENOME
( D ) DEVELOPMENTAL STAGE:
( E ) HAPLOTYPE:

-continued ( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: SEQUENCE FROM GP160

( x i ) SEQUENCE DESCRIPTION: SEQ ID NO: 32:

GAATTGGATA CGTGGGCA 18

( 2 ) INFORMATION FOR SEQ ID NO: 33:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: JS4/6
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: SEQUENCE FROM GP160

( x i ) SEQUENCE DESCRIPTION: SEQ ID NO: 33:

GCATTGGATA CGTGGGCA 18

( 2 ) INFORMATION FOR SEQ ID NO: 34:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: HIV-1
( B ) STRAIN:
( C ) INDIVIDUAL ISOLATE: SBB
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION:
( C ) IDENTIFICATION METHOD:
( D ) OTHER INFORMATION: SEQUENCE FROM GP160

( x i ) SEQUENCE DESCRIPTION: SEQ ID NO: 34:

-continued

AAGTTAGATG AGTGGGCA 18

( 2 ) INFORMATION FOR SEQ ID NO: 35:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION: RESIDUES 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 35:

TCGCTTGATA AGTGGGCC 18

( 2 ) INFORMATION FOR SEQ ID NO: 36:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION: RESIDUES 10-27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 36:

GGGCGTGATA AGTGGGCG 18

( 2 ) INFORMATION FOR SEQ ID NO: 37:

( i ) SEQUENCE CHARACTERISTICS:
( A ) LENGTH: 18
( B ) TYPE: NUCLEIC ACID
( C ) STRANDEDNESS: SINGLE ( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 37:

GGGGCTGATA AGTGGGCG 18

( 2 ) INFORMATION FOR SEQ ID NO: 38:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 38:

GCTCATGAAA AGTGGGCG 18

( 2 ) INFORMATION FOR SEQ ID NO: 39:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:

-continued ( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY:
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 39:

GCTTGTGATC AGTGGGCG 18

( 2 ) INFORMATION FOR SEQ ID NO: 40:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN
( B ) LOCATION: RESIDUES 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 40:

GGAGCTGATA AGTGGGGT 18

( 2 ) INFORMATION FOR SEQ ID NO: 41:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN
( B ) LOCATION: RESIDUE 10 TO 27

-continued ( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 41:

GGAGCTGATA AGTGGAAT 18

( 2 ) INFORMATION FOR SEQ ID NO: 42:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN GENE
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 42:

GGCGCTGATA AATGGTGT 18

( 2 ) INFORMATION FOR SEQ ID NO: 43:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN GENE
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 43:

GGCGCTGATA AATGGGTT 18

( 2 ) INFORMATION FOR SEQ ID NO: 44:

-continued ( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN GENE
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 44:

GGGGCTGATA AGTGGCAT 18

( 2 ) INFORMATION FOR SEQ ID NO: 45:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN GENE
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 45:

GGAGCTGATA AATGTCAT 18

( 2 ) INFORMATION FOR SEQ ID NO: 46:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN GENE
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 46:

GGAGCTGATA AATGTCAG 18

( 2 ) INFORMATION FOR SEQ ID NO: 47:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN GENE
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 47:

GCTTATGATA AGTGGAGT 18

( 2 ) INFORMATION FOR SEQ ID NO: 48:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:

-continued ( I ) ORGANELLE:

( i x ) FEATURE:
( A ) NAME/KEY: p3 FUSION PROTEIN GENE
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 48:

GCTTTTGATA AGTGGGTT 18

( 2 ) INFORMATION FOR SEQ ID NO: 49:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN GENE
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 49:

GGGCCTGATA AATGGGGT 18

( 2 ) INFORMATION FOR SEQ ID NO: 50:

( i ) SEQUENCE CHARACTERISTICS:
( A ) LENGTH: 18
( B ) TYPE: NUCLEIC ACID
( C ) STRANDEDNESS: SINGLE
( D ) TOPOLOGY: LINEAR ( i i ) MOLECULE TYPE: POLYNUCLEOTIDE ( i i i ) HYPOTHETICAL: No ( i v ) ORIGINAL SOURCE:
( A ) ORGANISM: FILAMENTOUS PHAGE fUSE5
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( i x ) FEATURE:
( A ) NAME/KEY: p3 FUSION PROTEIN GENE
( B ) LOCATION: RESIDUE 10 TO 27
( C ) IDENTIFICATION METHOD:
( D ) OTHER INFORMATION: POLYNUCLEOTIDE FROM RANDOM LIBRARY OF GENE CODING THE p3 FUSION PROTEIN ( x i ) SEQUENCE DESCRIPTION: SEQ ID NO: 50:

-continued

| | |
|---|---|
| GCTCGTGATA AGTGGGCG | 18 |